United States Patent

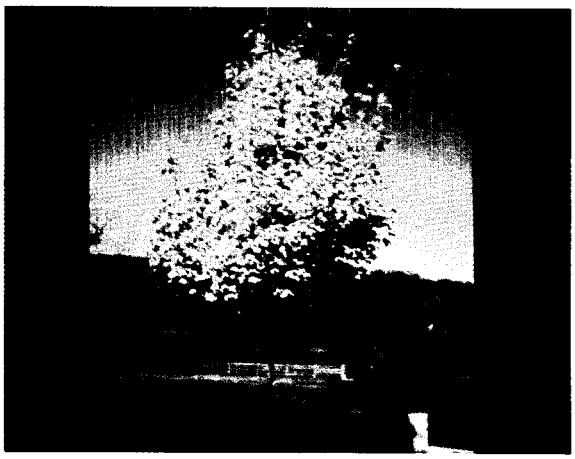
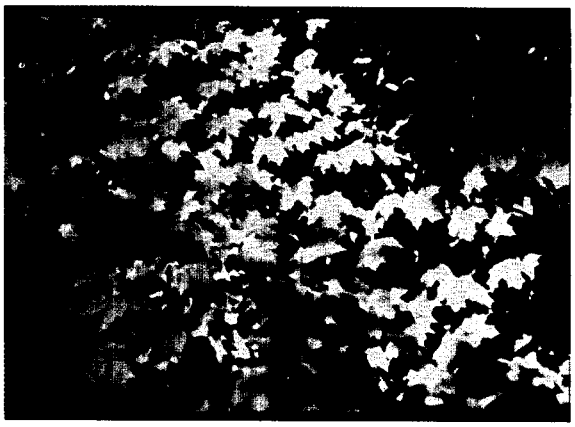
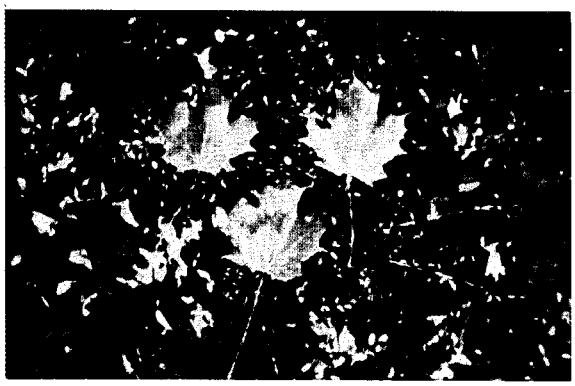

Plant Pat. 3,817

Patented Dec. 16, 1975

3,817

MAPLE TREE

William Flemer III, Princeton, N.J., assignor to Treesearch, Kingston, N.J.

Filed Dec. 4, 1974, Ser. No. 529,513

Int. Cl. A01h *5/00*

U.S. Cl. Plt.—51 1 Claim

The present invention relates to a new and distinct variety of maple tree of the species botanically known as *Acer saccharum* "columnare," which was originated by me in my nursery, located at South Brunswick Township, in the State of New Jersey.

At the time of my origination aforesaid, a block of seedlings were being grown under my care and supervision in the aforementioned nursery, from open-pollinated seed of *Acer saccharum* "columnare" which I had planted in the nursery. In the course of these growing and cultivating operations, my attention was attracted to one particular seedling in one row which was outstanding for its brilliant red autumn foliage color, contrary to the normal yellow or orange-yellow fall color of the leaves of all its sister seedlings in the same and adjacent rows. I therefore carefully preserved the distinctive seedling, and after several series of propagations by bud-grafting, as performed by me in my nursery aforesaid on an expanded scale (some 110 trees the first year, 427 trees the third year, etc.), I found that the bright red fall color proved to be fixed and fully established when the seedlings were grafted on random seedling understocks and grown in varying soil conditions, as compared with regular seedling trees in the same or adjacent rows.

Continued tests and prolonged observations conducted by me still further showed that the tree of my new red seedling is broad oval in shape, rather than open-headed, is one-third more rapid in growth than ordinary seedling sugar maples, and the young trees thereof, when grown in nursery rows, exhibit good resistance to terminal injury from the feeding activities of leaf hopper insects (Empoasca species).

In view of the foregoing, among other reasons, I am convinced that my new red seedling is a new and distinct variety, as particularly evidenced by the following unique combination of principal characteristics which are outstanding in the same and which distinguish it from all other varieties of which I am aware:

(1) A spreading, broad oval tree shape;
(2) A more rapid growing habit as compared to ordinary sugar maples;
(3) Good resistance to terminal injury from the feeding activities of leaf hopper insects, particularly when growing as young trees in nursery rows; and
(4) A distinctive and very attractive bright red leaf color during the fall season.

The accompanying drawing shows a typical specimen tree of my new variety, as well as close-up views of typical leaves, depicting the bright red fall color of the leaves which is the most outstanding feature of the new variety.

The following is a detailed description of my new variety of maple tree, with color terminology in accordance with the Munsell Color Chart, except where general color terms of ordinary dictionary significance are obvious, as based on observations made from specimen trees grown in my nursery in South Brunswick Township, N.J.:

Parentage: A selected cultivated seedling grown from open-pollinated seeds of *Acer saccharum* "columnare."

Propagation: Holds its distinguishing characteristics through succeeding propagations by bud-grafting.

Tree: Large; spreading, broad oval shape; tall; hardy; otherwise not substantially different in form from the average sugar maple.

*Trunk.*—Slender; smooth.

*Branches.*—Stocky; smooth. Color—Strong Brown, Plate 2.5YR4/7. Lenticels—Small; moderately abundant.

*Leaves.*—Medium thickness. Quantity—Moderately abundant. Size—Length of blade—About 13 cm. to 15 cm. Width of blade—About 13 cm. to 16 cm. Petiole—About 14 cm. to 16 cm. long. Shape—Palmate, with 3 major lobes and 8 minor lobes. Color (in fall)—Strong Red, Plate 5R4/12, suffused with Vivid Red, Plate 5R5/13. Glands—None.

Flower Buds: Inconspicuous.

Flowers: Not conspicuous.

*Petalage.*—Apetalous.

*Color.*—Strong Green-Yellow, Plate 2.5GY7/10.

Fruit: Paired winged sameness.

*Borne.*—From June to October in New Jersey.

*Abundance.*—Not abundant.

*Length.*—About 3.5 cm.

*Color.*—Pale brown.

Insect resistance: Good resistance to terminal injury from the feeding activities of leaf hopper insects (Empoasca species), particularly when growing as young trees in nursery rows as determined by comparison with other varieties grown under the same conditions in the same area of New Jersey.

I claim:

1. A new and distinct variety of maple tree of the species botanically known as *Acer saccharum* "columnare," substantially as herein shown and described, characterized particularly as to novelty by the unique combination of a spreading, broad oval tree shape; a more rapid growing habit as compared to ordinary sugar maples; good resistance to terminal injury from the feeding activities of leaf hopper insects, particularly when growing as young trees in nursery rows; and a distinctive and very attractive bright red leaf color during the fall season.

No references cited.

ROBERT E. BAGWILL, Primary Examiner